United States Patent [19]

Boutevin et al.

[11] Patent Number: 4,740,640
[45] Date of Patent: Apr. 26, 1988

[54] PERCHLOROFLUORINATED HYDROCARBONS AND PROCESS FOR THEIR PREPARATION

[75] Inventors: Bernard Boutevin; Yves Hervaud, both of Montpellier, France

[73] Assignee: Atochem, Courbevoie, France

[21] Appl. No.: 792,969

[22] Filed: Oct. 30, 1985

[30] Foreign Application Priority Data

Nov. 13, 1984 [FR] France .................. 84 17278

[51] Int. Cl.$^4$ .................. C07C 19/02; C07C 17/26; C07C 17/24; C07C
[52] U.S. Cl. .................. 570/134; 570/172
[58] Field of Search .................. 570/134, 172

[56] References Cited

U.S. PATENT DOCUMENTS 2,411,159 11/1949 Hanford .................. 570/172

OTHER PUBLICATIONS

Boutevin et al., Chemical Abstracts, 81, p. 356, item 49221j, 1974.

Primary Examiner—J. E. Evans
Attorney, Agent, or Firm—Brooks Haidt Haffner & Delahunty

[57] ABSTRACT

Novel perchlorofluorinated hydrocarbons of the general formula:

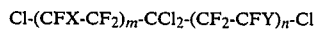

$$Cl\text{-}(CFX\text{-}CF_2)_m\text{-}CCl_2\text{-}(CF_2\text{-}CFY)_n\text{-}Cl$$

wherein X and Y represent chlorine or fluorine atoms, and m and n are integers from 1 to 5, together with a process for preparing such perchlorofluorocarbons by reacting chlorotrifluoroethylene or tetrafluoroethylene with carbon tetrachloride or a telomer having the formula $Cl_3C\text{-}(CF_2\text{-}CFX)_m\text{-}Cl$ in a polar solvent at a temperature of at least 120° C. in the presence of copper or a copper salt.

3 Claims, No Drawings

PERCHLOROFLUORINATED HYDROCARBONS AND PROCESS FOR THEIR PREPARATION

BACKGROUND OF THE INVENTION

The present invention relates to perhalogenated hydrocarbons, and more particularly, it relates to novel perchlorofluorinated hydrocarbons and a process for their preparation.

In the perhalogenated hydrocarbon series, and particularly the perchlorofluorocarbons, the lower members have been known for a long time and are widely used in many fields, such as aerosol packaging, refrigeration, manufacture of plastic foams, cleaning, and the like.

The less volatile perchlorofluorinated hydrocarbons are known. Examples of these include telomers of chlorotrifluoroethylene or tetrafluoroethylene with carbon tetrachloride. See, for example, Tetrahedron Letters 12, 887 (1973); Eur. Polym. J. 12, 219 (1976); J. Am. Chem. Soc. 83, 3425 (1961); European Patent No. 93580; and British Patents Nos. 1,007,542 and 1,127,045. These telomers are valuable intermediates for the synthesis of functional chlorofluorinated compounds which can be used in the preparation of polymers with hydrophobic and oleophobic properties. The conversion of these telomers to chlorofluorinated acids and alcohols has been studied in particular by Boutevin et al. in Tetrahedron Letters 12, 939 (1974); Eur. Polym. J. 12, 231 (1976); and Makromol. Chem. 182, 2927 (1981).

THE INVENTION

It has now been found that it is possible to obtain from these telomers new perchlorofluorinated hydrocarbons having the general formula:

$$Cl\text{-}(CFX\text{-}CF_2)_m\text{-}CCl_2\text{-}(CF_2\text{-}CFY)_n\text{-}Cl \quad (I)$$

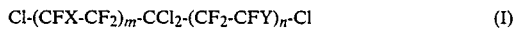

in which X and Y can be the same or different and represent a chlorine or fluorine atom, and m and n are the same or different integers from 1 to 5. In certain preferred embodiments, m and n are one.

The compounds of formula (I) according to the invention are obtained by reacting chlorotrifluoroethylene or tetrafluoroethylene with a telomer having the formula:

$$Cl_3C\text{-}(CF_2\text{-}CFX)_m\text{-}Cl \quad (II)$$

in which X and m have the same meaning as above, in an organic polar solvent other than an alcohol at a temperature of at least 120° C. in the presence of copper and/or copper salt catalyst.

In certain embodiments of this invention, the polar solvents or vehicles are nitriles such as acetonitrile, butyronitrile or isobutyronitrile; ethers such as tetrahydrofuran; and amides such as dimethylformamide. The amount of solvent can vary over a wide range. In order to limit the pressure in the reactor, however, it is desirable to use 0.5 to 5 moles of solvent per mole of the chlorotrifluoroethylene or tetrafluoroethylene monomer. In certain preferred embodiments, two moles of solvent are used per mole of monomer.

The catalyst can have the copper in the $Cu^o$, $Cu^+$ and/or $Cu^{++}$ state. Although it is preferred to use the copper in the form of a chloride, the nature of the anion is relatively unimportant. The amount copper and/or copper salt to be used per mole of monomer can vary from $5 \times 10^{-3}$ to $5 \times 10^{-2}$ mole and is preferably about $1 \times 10^{-2}$ mole. When n is smaller, the amount of catalyst used is greater.

The reaction of this invention is carried out at a temperature of at least 120° C. Although it is preferred to operate at approximately 140° C. to limit the pressure in the reactor, it is possible to work at higher temperatures, up to approximately 180° C.

The molar ratio of monomer to telomer can be from one to 15 as a function of quantity of compound required, (I), the value of n increasing in the same direction.

The compounds of formula (I) according to the invention in which X and Y are the same can also be obtained by reacting chlorotrifluoroethylene or tetrafluoroethylene with carbon tetrachloride under the same conditions as above, but with a molar ratio of the chlorotrifluoroethylene or tetrafluoroethylene to carbon tetrachloride being at least two and in certain preferred embodiments from two to 20, the value of (m+n) increasing in the same direction. As the value of (m+n) decreases, the amount of catalyst used is greater.

The compounds of formula (I) produced according to this invention are valuable intermediates for the synthesis of functional chlorofluorinated compounds which can be used as surfactants or as raw materials in the preparation of polymers with hydrophobic and lipophobic properties. Like the telomers from which they are derived, the compounds according to the invention can in particular be readily converted to acids and then to alcohols by known methods, such as those described by Boutevin et al. in the afore-mentioned references.

All parts, percentages, proportions, and ratios herein are by weight unless otherwise stated.

The following Examples are given to illustrate embodiments of the invention as it is presently preferred to practice it. It will be understood that these Examples are illustrative, and the invention is not to be considered as restricted thereto except as indicated in the appended claims.

The $^{19}F$ NMR spectra in these Examples are obtained on a Varian E.M. 390 apparatus at a frequency of 84.67 MHz using $CFCl_3$ as the reference. The mass spectra are obtained with a CEC 211 10C (double focusing) apparatus equipped with an ionization source (100 μA, 70 e.v.) and a direct introduction system. The m/e values and, in parentheses, the percentage relating to each peak with respect to the base peak, are shown.

EXAMPLE I (a) A 4.5-liter glass-lined steel pot autoclave (Pfaudler reactor) equipped with apparatus for oil circulation heating, a variable-speed stirring system, and a valve for introducing gas, is charged with 1.54 kg (10 moles) of carbon tetrachloride, followed by 13.45 g (0.1 mole) of copper chloride dissolved in a half-liter of acetonitrile. After the reactor is closed, 1.165 kg (10 moles) of chlorotrifluoroethylene is introduced, and the mixture is heated at 120° C. for 24 hours with stirring at 200 rpm.

After washing the mixture with acidified water to remove the copper and distilling it under vacuum (20 torr), 2.57 kg of the telomer $CFCl_2\text{-}CF_2CCl_3$ (B.P. 47° C. at 15 ton) is obtained.

(b) The same reactor as above is charged with 2.705 kg (10 moles) of $CFCl_2\text{-}CF_2CCl_{13}$ telomer and 13.5 g (0.1 mole) of copper chloride dissolved in one liter of acetonitrile. The reactor is closed, 1.165 kg (10 moles) of chlorotrifluoroethylene are introduced, and the mixture is then heated at 140° C. for 48 hours with stirring at 200 rpm. By distillation in vacuo, 1,1,3,3,5,5-hexachloro-1,2,2,4,4,5-hexafluoropentane, boiling at 97° C. under 15 mm Hg, is obtained in a yield of 60%.

|  | C % | Cl % | F % |
| --- | --- | --- | --- |
| Calculated for $C_5Cl_6F_6$ | 15.50 | 55.04 | 29.46 |
| Found | 15.92 | 55.78 | 28.07 |

$^{19}F$ NMR spectrum: Band (2F) centered at $64.33 \times 10^{-6}$, Band (4F) centered at $101 \times 10^{-6}$.

Mass spectrum: 357(2.5); 355(4); 353(6); 351(5); 349(4); 301(2.5); 299(5); 297(11); 295(7.5); 252(2,5); 250(5); 248(4); 239(15); 237(40); 235(67); 233(60); 221(18); 219(32); 217(35); 153(18); 151(25); 105(18); 103(68); 101(100); 85(28).

EXAMPLE II

In a Pyrex Carius tube (thickness: 2 mm, length: 260 mm, diameter: 23 mm), 99 mg of cuprous chloride, 38.7 g (0.1 mole) of the $CCl_3$-$(CF_2CFCl)_2Cl$ telomer described by Boutevin and Pietrasanta [Eur. Polym. J. 12, 219 (1976)], and 10 ml of acetonitrile are admixed. The tube is cooled in an acetone/solid carbon dioxide mixture, 11.65 g (0.1 mole) of chlorotrifluoroethylene are then introduced, and the tube is sealed. The sealed tube is heated for 16 hours at 180° C. in an autoclave agitated by rocking.

After the tube is opened, the reaction product is washed with a dilute solution of HCl to remove the copper, extracted with ether and distilled in vacuo to provide 13.6 g of 1,1,3,3,5,7,7-heptachloro-1,2,2,4,4,5,6,6,7-nonafluoroheptane, boiling at 97° C. under 0.1 mm Hg. The chlorine content is 49.01% (calculated for $C_7Cl_7F_9$: 49.35%).

$^{19}F$ NMR Spectrum: Band (1F) centered at $125 \times 10^{-6}$, Band (2F) centered at $108.8 \times 10^{-6}$, Band (4F) between 97 and $106 \times 10^{-6}$, Band (1F) centered at $67 \times 10^{-6}$, Band (1F) centered at $64.7 \times 10^{-6}$.

Mass spectrum: 473(0.4); 471(0.8); 469(1.5); 467(2); 465(1); 417(1); 415(4); 413(6); 411(4); 357(1); 355(4); 353(8); 351(12); 349(8); 399(0.5); 297(4); 295(3); 283(1); 281(1); 279(4) 271(3); 269(9); 267(10); 253(1); 251(5); 249(4); 239(4); 237(16); 235(26); 233(22); 185(1); 183(1); 179(12); 167(4165(17); 163(16); 155(6); 153(18); 151(26); 105(18); 103(70); 101(100); 87(22); 85(62); 69(20).

EXAMPLE III

The same autocalve as in Example I is charged with 1.54 kg (10 moles) of carbon tetrachloride, followed by 26.9 g (0.2 moles) of copper chloride dissolved in 1.5 liters of acetonitrile, and 2.330 kg (20 moles) of chlorotrifluoroethylene.

After 24 hours of heating at 140° C. with stirring at 200 rpm, 3.280 kg of a mixture of $CFCl_2$-$CF_2$-$CCl_3$ and $CFCl_2$-$CF_2$-$CCl_2$-$CF_2$-$CFCl_2$ in the weight ratio of 70/30 is obtained. After 48 hours of heating at 140° C., 3.400 kg of the same mixture in the weight ratio of 50/50 is obtained.

The products are identified as in the previous Examples.

What is claimed is:

1. Perchlorofluorocarbons having the formula:

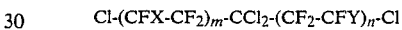

Cl-(CFX-CF$_2$)$_m$-CCl$_2$-(CF$_2$-CFY)$_n$-Cl wherein X and Y are chlorine and m and n are the same or different integers from one to five, inclusive.

2. The 1,1,3,3,5,5-hexachloro-1,2,2,4,4,5-hexafluoropentane according to claim 1.

3. The 1,1,3,3,5,7,7-heptachloro-1,2,2,4,4,5,6,6,7-nonafluoroheptane according to claim 1.

* * * * *